(12) United States Patent
Pauli et al.

(10) Patent No.: US 8,852,086 B2
(45) Date of Patent: Oct. 7, 2014

(54) ENDOSCOPE WITH VARIABLE DIRECTION OF VIEW

(75) Inventors: Sabine Pauli, Seitingen-Oberflacht (DE); Oliver Rehe, Tuttlingen (DE)

(73) Assignee: Henke-Sass, Wolf GmbH, Tuttlingen (DE)

( * ) Notice: Subject to any disclaimer, the term of this patent is extended or adjusted under 35 U.S.C. 154(b) by 311 days.

(21) Appl. No.: 13/234,434

(22) Filed: Sep. 16, 2011

(65) Prior Publication Data
US 2012/0078049 A1 Mar. 29, 2012

(30) Foreign Application Priority Data
Sep. 17, 2010 (DE) .......................... 10 2010 040 992

(51) Int. Cl.
- A61B 1/06 (2006.01)
- A61B 1/267 (2006.01)
- A61B 1/00 (2006.01)
- G02B 26/08 (2006.01)
- G02B 23/24 (2006.01)

(52) U.S. Cl.
CPC ......... A61B 1/00096 (2013.01); A61B 1/00066 (2013.01); G02B 26/0883 (2013.01); A61B 1/00183 (2013.01); G02B 23/2423 (2013.01)
USPC ............ 600/173; 600/170; 600/171; 600/189

(58) Field of Classification Search
CPC .............................. A61B 1/00183; A61B 1/05
USPC ......... 600/173, 170, 171, 176, 445, 118, 103, 600/101, 189
See application file for complete search history.

(56) References Cited

U.S. PATENT DOCUMENTS

| | | | | |
|---|---|---|---|---|
| 3,856,000 A * | 12/1974 | Chikama | | 600/173 |
| 3,918,438 A * | 11/1975 | Hayamizu et al. | | 600/168 |
| 4,697,577 A * | 10/1987 | Forkner | | 600/173 |
| 4,760,840 A * | 8/1988 | Fournier et al. | | 606/15 |
| 5,222,482 A * | 6/1993 | Clark | | 600/111 |
| 5,575,754 A * | 11/1996 | Konomura | | 600/117 |
| 5,588,948 A * | 12/1996 | Takahashi et al. | | 600/111 |
| 5,689,365 A * | 11/1997 | Takahashi | | 359/362 |
| 5,720,706 A * | 2/1998 | Takahashi et al. | | 600/111 |
| 6,110,105 A * | 8/2000 | Durell | | 600/173 |
| 6,364,830 B1 * | 4/2002 | Durell | | 600/173 |
| 6,371,909 B1 * | 4/2002 | Hoeg et al. | | 600/173 |
| 6,428,471 B1 * | 8/2002 | Durell, Jr. | | 600/173 |
| 6,500,115 B2 * | 12/2002 | Krattiger et al. | | 600/173 |

(Continued)

FOREIGN PATENT DOCUMENTS

DE 10 2009 049 14 12/2010
WO WO2011/044878 A1 4/2011

*Primary Examiner* — John P Leubecker
*Assistant Examiner* — Ronald D Colque
(74) *Attorney, Agent, or Firm* — Skaar Ulbrich Macari, P.A.

(57) ABSTRACT

Provided is an endoscope with a handle, an endoscope shaft connected to the handle, and imaging optics arranged in the endoscope shaft. An object can be located in the direction of view of the imaging optics in front of the endoscope shaft. The endoscope may also include a swivellably housed deflecting element that sets the desired direction of view. The deflecting element can be positioned at the distal end of the endoscope shaft facing away from the handle. An actuating element can be attached to the handle, which is mechanically connected to the deflecting element, and with which the swivel position of the deflecting element can be changed in order to set a desired direction of view.

14 Claims, 5 Drawing Sheets

(56) References Cited

U.S. PATENT DOCUMENTS

| | | | |
|---|---|---|---|
| 6,537,210 B1 * | 3/2003 | Wulfsberg | 600/173 |
| 6,638,216 B1 * | 10/2003 | Durell | 600/173 |
| 6,648,817 B2 * | 11/2003 | Schara et al. | 600/173 |
| 6,695,774 B2 * | 2/2004 | Hale et al. | 600/173 |
| 7,018,330 B2 * | 3/2006 | Alekseenko et al. | 600/130 |
| 7,160,248 B2 * | 1/2007 | Alekseenko et al. | 600/130 |
| 7,175,593 B2 * | 2/2007 | Durell | 600/173 |
| 7,344,494 B2 * | 3/2008 | Hoeg et al. | 600/173 |
| 7,374,533 B2 * | 5/2008 | Hoeg et al. | 600/173 |
| 7,427,263 B2 * | 9/2008 | Hoeg et al. | 600/173 |
| 7,553,277 B2 * | 6/2009 | Hoefig et al. | 600/173 |
| 7,625,335 B2 * | 12/2009 | Deichmann et al. | 600/117 |
| 7,896,803 B2 * | 3/2011 | Schara et al. | 600/173 |
| 8,485,968 B2 * | 7/2013 | Weimer et al. | 600/173 |
| 2001/0018553 A1 * | 8/2001 | Krattiger et al. | 600/173 |
| 2002/0049366 A1 * | 4/2002 | Kehr | 600/172 |
| 2002/0082476 A1 * | 6/2002 | Takahashi et al. | 600/173 |
| 2003/0092966 A1 * | 5/2003 | Schara et al. | 600/173 |
| 2003/0233029 A1 * | 12/2003 | Alekseenko et al. | 600/173 |
| 2004/0015049 A1 * | 1/2004 | Zaar | 600/101 |
| 2004/0097791 A1 * | 5/2004 | Tokuda et al. | 600/173 |
| 2004/0236183 A1 * | 11/2004 | Durell | 600/173 |
| 2005/0085698 A1 * | 4/2005 | Bonningue et al. | 600/170 |
| 2006/0129032 A1 * | 6/2006 | Durell | 600/173 |
| 2007/0055103 A1 * | 3/2007 | Hoefig et al. | 600/173 |
| 2010/0010302 A1 * | 1/2010 | Hadani | 600/109 |
| 2010/0030031 A1 * | 2/2010 | Goldfarb et al. | 600/163 |

* cited by examiner

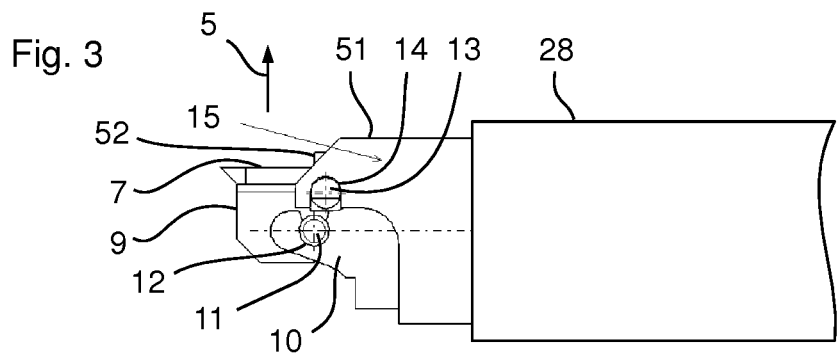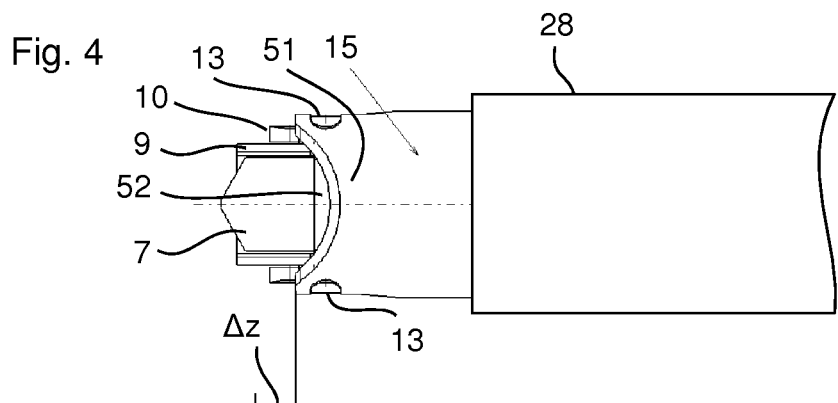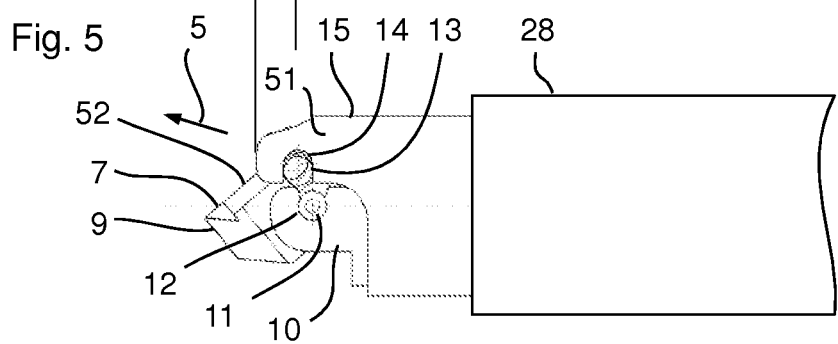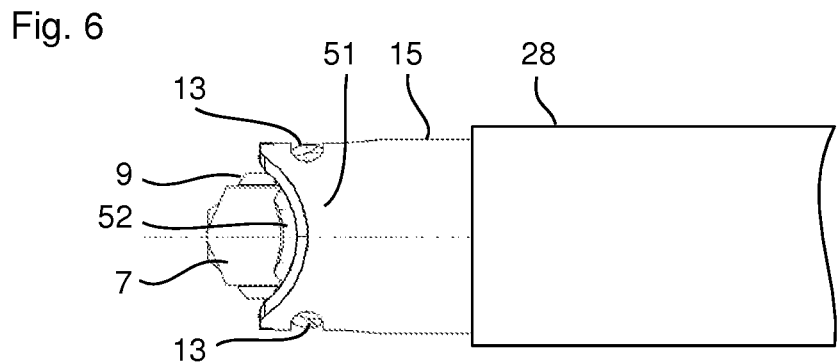

ENDOSCOPE WITH VARIABLE DIRECTION OF VIEW

PRIORITY

The present application claims priority to German Application No. 102010040992.8, filed Sep. 17, 2010, which is hereby incorporated by reference in its entirety.

FIELD

The invention relates to endoscopes, and more particularly, to endoscopes with a variable direction of view.

BACKGROUND

Endoscopes with a variable direction of view frequently have at the distal end of the endoscope shaft a swivellably housed deflecting element as part of the imaging optics in order to set the desired direction of view by means of the swivel position of the deflecting element. With conventional endoscopes, the swivel position is set, for example, by means of a rotating wheel provided on the handle of the endoscope. The set swivel position can be seen by the position of the rotating wheel. A disadvantage of this is that, when observing the object displayed by means of the imaging optics of the endoscope (thus when observing the image produced by means of the imaging optics), the user can no longer see what rotation position the rotating wheel occupies and thus, when observing the image, does not see just which direction of view is set.

SUMMARY

It is an object of certain embodiments of the invention to provide an endoscope with variable direction of view in which, when observing the image of the imaging optics, the set direction of view is displayed.

In certain embodiments, as the first marking stop is mechanically connected to the actuating element such that it is moved synchronously with a change in the swivel position of the deflecting element and displays the set direction of view by means of its visible position when observing the image, the set direction of view can always be represented simply in the image. Thus, when observing the image, a user is also always provided visually with the information as to just which direction of view is set.

The actuating element can be rotatably housed on the handle. In particular, it is housed rotatable about the longitudinal axis of the endoscope shaft. This makes it easier to operate the endoscope.

Furthermore, with the endoscope according to certain embodiments of the invention, the endoscope shaft can be rotatably housed on the handle and the endoscope can have a second marking stop which is connected in rotation-resistant manner to the endoscope shaft and which, by means of its visual position when observing the image, displays the rotation position of the endoscope shaft. Thus the observer is advantageously visually provided with the direction of the view of the endoscope and also the rotation position of the endoscope shaft when he observes the image of the imaging optics.

The set direction of view can be displayed via the position of the first marking stop relative to the position of the second marking stop when observing the image. Thus e.g. the angular separation between the two marking stops can be varied in order to display the direction of view. In particular the angular separation between the two marking stops can correspond to the set direction of view (for example relative to the longitudinal direction of the endoscope shaft). Thus it is very easy for the observer to see just which direction of view is set.

With the endoscope according to certain embodiments of the invention, the actuating element can be connected to the first marking stop via a reduction gear mechanism. Thus it is advantageously achieved that the movement (for example rotation) of the first marking stop is smaller than the corresponding movement of the actuating element. The reduction gear mechanism can convert a rotation of the actuating element into an axial movement and the axial movement into a rotational movement of the first marking stop. This can easily be produced mechanically with the desired precision.

The first marking stop can be positioned in the area of the field stop of the imaging optics. The second marking stop can also be positioned in the area of the field stop of the imaging stop. The first marking stop can be housed rotatable relative to the imaging optics. In particular the first marking stop can be configured on a rotatably housed sleeve which e.g. is arranged coaxially to the longitudinal direction or axis of the endoscope shaft.

The endoscope according to certain embodiments of the invention can be an endoscope with a rigid endoscope shaft. However, it is also possible that the endoscope shaft is configured such that at least sections of it can be bent out. The distal end of the endoscope shaft can be sealed with a cover glass. In particular the distal end can be hermetically sealed, with the result that the endoscope shaft can be autoclaved.

The swivellable deflecting element can be a deflecting mirror or a deflecting prism. The deflecting element can be fixed in a rotatably housed holder, wherein the axis of rotation of the holder preferably lies perpendicular to the longitudinal direction of the endoscope shaft. The holder can be rotated about its axis of rotation via a draw tube (which can also be called sliding element) arranged in the endoscope shaft. For this, the proximal end of the draw tube can be moved axially by means of the actuating element. In particular, the actuating element can be mechanically connected to the draw tube via a first gear mechanism. The first gear mechanism can be configured such that it converts a rotational movement of the actuating element into an axial movement of the draw tube.

The distal end of the draw tube can in particular be configured such that it forms a baffle (which can also be called screening section) which ensures, irrespective of the set swivel position of the holder of the deflecting element, that no undesired scattered light passes between the deflecting element and the following optical element in the imaging optics. For this, the distal end of the draw tube is preferably mechanically connected directly to the holder of the deflecting element. Advantageously, this leads to the swivel position of the deflecting element being set by means of the draw tube and, simultaneously, also the baffle (distal end section of the draw tube) being positioned such that the endoscope can be used without time delay when there is a change in the direction of view. It is no longer necessary, as previously, to position the baffle separately after setting the direction of view.

With the endoscope according to certain embodiments of the invention, to connect the distal end of the sliding element to the deflecting element an actuating pin is provided as first connecting element and a receptacle guiding the actuating pin as second connecting element, wherein one of the two connecting elements is provided at the deflecting element and the other of the two connecting elements at the sliding element. The actuating pin ban be provided at the deflecting element itself or at a holder in which the deflecting element sits.

A further illumination channel can be provided in the endoscope shaft via which the object to be imaged can be illuminated. Illumination can take place for example by means of optical fibers which can be impacted by light at the handle. Naturally other types of illumination are also possible. In particular, a light source (e.g. one or more LED diodes) can be provided for illumination at the distal end of the endoscope shaft.

It is understood that the features mentioned above and those yet to be explained below can be used, not only in the stated combinations, but also in other combinations or alone, without departing from the scope of the present invention.

BRIEF DESCRIPTION OF THE DRAWINGS

The invention is explained in further detail below by way of example using the attached drawings which also disclose features essential to the invention. There are shown in:

FIG. 3 is an enlarged lateral view of the distal end of the endoscope shaft with a first swivel position of the deflecting prism;

FIG. 4 is a top view of the distal end of the endoscope shaft according to FIG. 3;

FIG. 5 is an enlarged lateral view of the distal end of the endoscope shaft with a second swivel position of the deflecting prism;

FIG. 6 is a top view of the distal end of the endoscope shaft according to FIG. 5;

DETAILED DESCRIPTION

In the following descriptions, the present invention will be explained with reference to example embodiments thereof. However, these example embodiments are not intended to limit the present invention to any specific example, environment, embodiment, applications or particular implementations described in these example embodiments. Therefore, descriptions of these example embodiments are only for purposes of illustration rather than limitation to the invention. It should be appreciated that in the following example embodiments and the attached drawings, elements unrelated to the present invention are omitted from depiction; and dimensional relationships among individual elements in the attached drawings are illustrated only for ease of understanding, but not to limit the actual scale.

Figure 1:
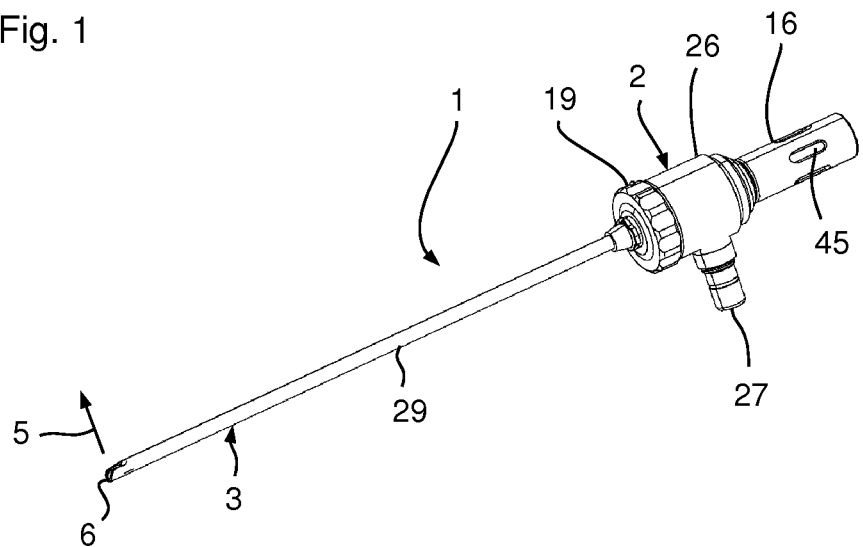
FIG. 1 is a schematic perspective view of an embodiment of the endoscope according to the invention.

With the embodiment shown in FIG. 1 the endoscope according to the invention 1 with variable direction of view comprises a handle 2 and an endoscope shaft 3, the casing tube 29 of which can be seen in FIG. 1, connected to the handle 2.

Figure 2:
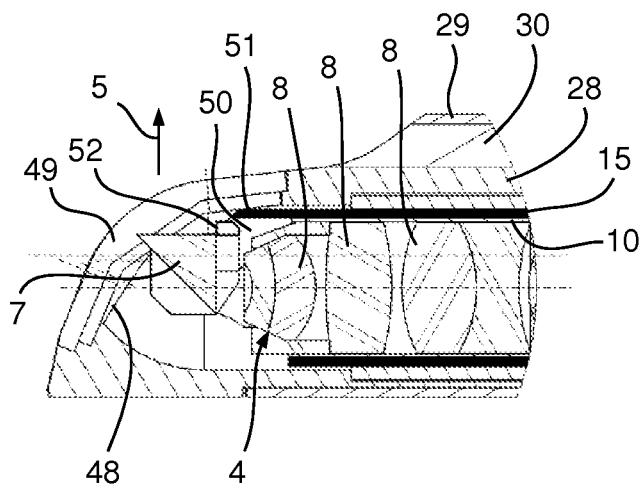
FIG. 2 is an enlarged sectional representation of the distal end of the endoscope shaft from FIG. 1.

As can be seen in particular from the enlarged sectional representation of the distal end 6 of the endoscope shaft 3 in FIG. 2, imaging optics 4 with which an object located in the direction of view 5 of the imaging optics 4 in front of the endoscope shaft 3 can be displayed as an image are arranged in the endoscope shaft 3.

The imaging optics 4 comprise a deflecting prism 7 as well as lenses 8 arranged downstream of this. The deflecting prism 7 sits in a prism holder 9 which is swivellably housed at the distal end of an optics tube 10 arranged in an endoscope shaft 3, as is best seen in the enlarged lateral view and top view of the distal end 6 of the endoscope shaft 3 in FIGS. 3 and 4 wherein, with the representations in FIGS. 3 and 4, in each case, the casing tube 29 is not drawn in.

For the swivellable housing, the prism holder 9 has two bearing pins 11 forming a swivel axis which sit in corresponding receptacles 12 of the distal end of the optics tube 10 (only the left-hand bearing pin 11 and the left-hand receptacle 12 can be seen in FIG. 3).

The prism holder 9 also has two actuating pins 13 which sit in receptacles 14 of a draw tube 15 in which optics tube 10 is positioned. The draw tube 15 is housed displaceable relative to the optics tube 10 and to the casing tube 29 in longitudinal direction of the endoscope shaft 3, wherein the axial position of the draw tube 15 can be set by means of an actuating element 16 (FIG. 1) attached to the handle 2, as is further described below in detail.

The same views as in FIGS. 3 and 4 are shown in FIGS. 5 and 6, wherein however the draw tube 15 is axially displaced compared with FIGS. 3 and 4. The axial displacement is drawn in as ⊡ z between FIGS. 4 and 5. As a comparison of the representations of FIGS. 3 and 4 with those of FIGS. 5 and 6 shows, an axial displacement of the draw tube 15 causes the actuating pins 13 to move around the bearing pins 11 at the distance from these predetermined by the design. The actuating pins 13 are thus moved on an orbit lying in the drawing plane of FIGS. 3 and 5, the centre of which is the bearing pins 11 and thus the point where the swivel axis pierces the drawing plane of FIGS. 3 and 5. This movement of the actuating pins 13 is possible as they are housed displaceable in the receptacles 14 of the distal end of the draw tube 15 (displaceable from top to bottom viewed in FIGS. 3 and 5).

Thus the axial displacement of the draw tube 15 leads to a swivelling of the prism holder 9 about the swivel axis defined by the bearing pins 11 which runs perpendicular to the drawing plane in FIGS. 3 and 5, and thus to a swivelling of the deflecting prism 7, whereby the direction of view 5 of the imaging optics 4 is changed. Thus the direction of view 5 in the representation from FIGS. 3 and 4 is approx. 90° (relative to the longitudinal direction of the endoscope shaft 3 which in each case lies in the drawing plane of FIGS. 3 to 6 and runs from left to right). In FIGS. 5 and 6 the direction of view 5 is, in contrast, approx. 10°.

The draw tube 15 or the distal end of the draw tube 15 can be configured such that it serves simultaneously as movable baffle which with each swivel position of the deflecting prism 7 prevents with certainty undesired scattered light from reaching the area 50 (FIG. 2) between the prism holder 9 and the lenses 8 of the imaging optics 4, which would lead to an undesired impairment of the imaging quality of the imaging optics 4. For this the draw tube 15 has a distal top screening section 51 which is always positioned above the rear part 52 of the prism holder 9, as is schematically represented in FIG. 2 and also in the different swivel positions according to FIGS. 3 to 6. It is thereby guaranteed that, irrespective of the set swivel position of the deflecting prism 7, no scattered light enters the area 50. The draw tube 15 thus serves to screen the undesired scattered light and at the same time drives the deflecting prism 7 to set the desired swivel position and thus to set the desired direction of view 5. Thus, after setting a new swivel position the endoscopes can be used without time delay, as the penetration of scattered light is always prevented with certainty. The imaging optics 4 are thus always shielded from direct scattered light irradiation.

Figure 7:
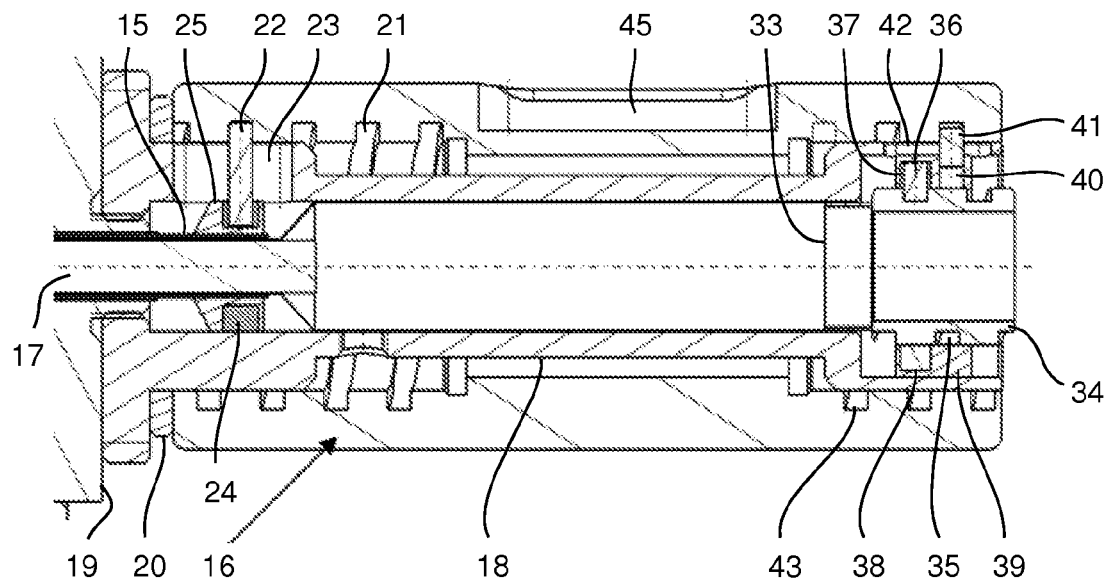
FIG. 7 is an enlarged sectional view of the proximal end of the handle of the endoscope according to FIG. 1.

The imaging optics 4 also have an image-transmission system (here in the form of rod lenses, one of which can be seen in the enlarged sectional representation of the proximal section of the handle 2 in FIG. 7) in the endoscope shaft 3 and in the handle 2 which serves to transmit the received image up to the proximal end of the handle where it is then made available. The image made available can be observed directly or via a proximally arranged eyepiece. It is also possible to attach for example a video camera which records the image and can display it via an output device (for example a monitor) to the proximal end of the handle 2.

As can be seen from the enlarged sectional representation of the proximal section of the handle 2 in FIG. 7, the actuating element 16 is designed in the form of a sleeve and rotatably housed on a guide sleeve 18 which for its part is connected in rotation-resistant manner to a main part 19 of the handle 2. A sliding disk 20 is provided between the distal end of the actuating element 16 and the guide sleeve 18.

On its inside, the actuating element 16 has in the distal area a first helical groove 21 into which the top end of a first bolt 22 projects. The first bolt 22 extends through a first oblong hole 23 extending in longitudinal direction of the endoscope shaft 3 (and thus from right to left in FIG. 7) of the guide sleeve 18 and is fixed at its bottom via a first Teflon ring 24 in a connecting part 25 which is connected in rotation-resistant manner to the proximal end of the draw tube 15.

Because of this structure, a rotation of the actuating element 16 about the longitudinal axis of the endoscope and relative to the main part 19 leads to the first bolt 22 being moved in axial direction (due to being guided through the first oblong hole 23 in the guide sleeve 18 connected in rotation-resistant manner to the main part 19), with the result that the connecting part 25 and thus the draw tube 15 are axially displaced. At the distal end of the draw tube 15 this displacement leads, as is represented in FIGS. 3 to 6, to a desired swivel position of the deflecting prism 7 being set.

The handle 2 also comprises a middle section 26 with an optical-fibre connection 27 (FIG. 1). The middle section 26 is connected to the endoscope shaft 3 in rotation-resistant manner and can be rotated about the longitudinal axis of the endoscope shaft 3 relative to the main part 19. For this, the endoscope shaft 3 is rotatably guided in the main part 19.

The endoscope shaft 3 also comprises as can best be seen from FIG. 2 an inner tube 28 in which the draw tube 15, the optics tube 10 and the imaging optics 4 are arranged, and the casing tube 29, in which the inner tube 28 is inserted. The inner diameter of the casing tube 29 is larger than the outer diameter of the inner tube 28, with the result that there is a space 30 extending along the longitudinal direction of the endoscope shaft 3 between the two tubes 28 and 29. Optical fibers (not shown in FIG. 2) which serve to illuminate the object to be displayed are arranged in the space 30. The optical fibers can be impacted by light via the optical-fibre connection 27 at the middle section 26. The casing tube 29 has a distal opening 48 which is closed (preferably hermetically sealed) by means of a glass cover 49, with the result that the imaging optics 4 are protected against dirt.

Figure 8:
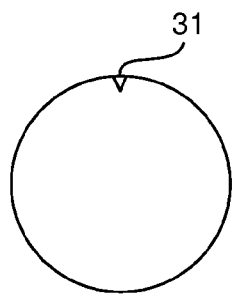
FIGS. 8 and 9 are representations explaining the fixed marking stop.
Figure 9:
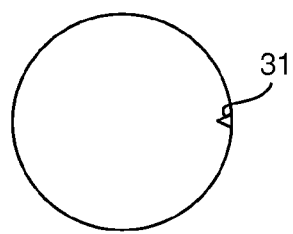

In order that the user can optically detect the rotation position of the endoscope shaft, when he observes the image produced by the imaging optics 4, a fixed marking sleeve 33 with a fixed marking stop 31 is connected in rotation-resistant manner to the optics tube 10 at the proximal end of the optics tube (FIG. 7). Here, the fixed marking stop 31 has the form of a triangle, as schematically represented in FIG. 8. If the user rotates the endoscope shaft 90° to the right (by rotating the middle section 26 relative to the main part 19), the fixed marking sleeve 33 moves and thus the fixed marking stop 31 with it, with the result that the user sees the marking stop in the position shown in FIG. 9 together with the image.

Figure 10:
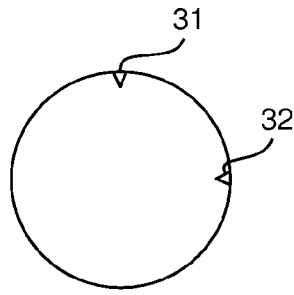
FIGS. 10 and 11 are representations explaining the fixed and rotatable marking stop.
Figure 11:
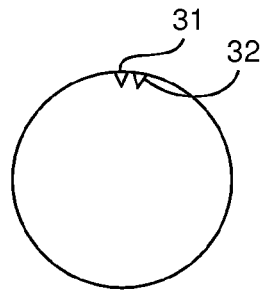

However, in the embodiment described here of the endoscope according to the invention, not only is a fixed marking stop 31 provided but also a further rotatable marking stop 32, which further displays in the image the direction of view 5 of the imaging optics 4 and thus the swivel position of the deflecting prism 7. The rotatable marking stop 32 can have the same form (for example triangular form) as the fixed marking stop 31, as shown schematically in FIG. 10. The case is shown in FIG. 10 where the swivel position of the prism corresponds to approx. 90°. If the swivel position shown in FIGS. 5 and 6 is set (direction of view of approx. 10°), the position of the rotatable marking stop 32 changes relative to the fixed marking stop 31 as represented in FIG. 11. Thus, when observing the image via the angle of rotation between both marking stops 31 and 32, the user sees the set swivel position of the deflecting prism and therefore the set direction of view 5. Naturally, the two marking stops 31 and 32 are preferably designed such that they can be distinguished clearly. Thus the two marking stops 31 and 32 can have different colours. Additionally, or alternatively, the two marking stops 31, 32 can have different forms.

Figure 12:
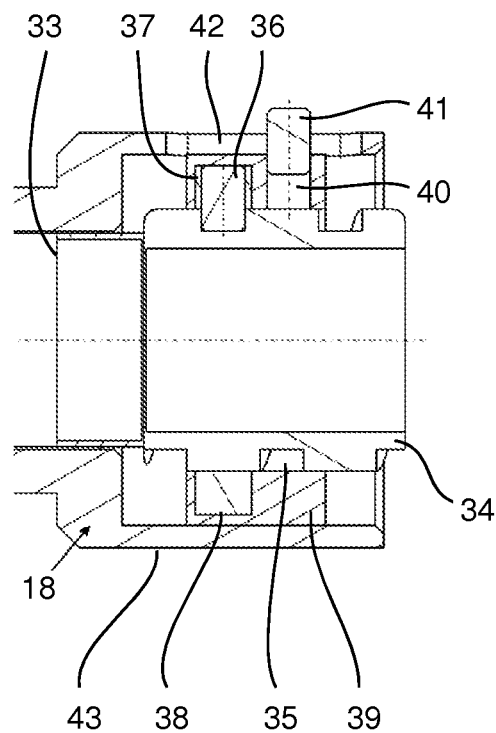
FIG. 12 is an enlarged sectional representation of the right-hand side of FIG. 7 without actuating element.

The rotatable marking stop 32 is secured on the inside of a rotatable marking sleeve 34 (FIG. 7) such that it lies in the field of vision of the represented image. The rotatable marking sleeve 34 has on its outside a helical groove 35 into which a first pin 36 projects, as can be seen from FIG. 7 as well as from the enlarged detailed representation in FIG. 12.

The first pin 36 is firmly connected to a Teflon ring 37 which sits rotatable in an annular inner groove 38 of a sliding sleeve 39. The sliding sleeve 39 has a bore 40, axially spaced apart from the inner groove 38, in which a second pin 41 sits which projects through a second oblong hole 42 which extends in longitudinal direction of the endoscope shaft 3 of the guide sleeve 18. The top end of the second pin 41 opens into a groove 43 which is designed on the inside of the actuating element 16 and extends helically in the proximal area of the actuating element 16.

Because of this structure a rotation of the actuating element 16 relative to the guiding sleeve 18 leads to the rotational movement of the actuating element 16 being converted into an axial movement of the second pin 41 because of the second oblong hole 42. The axial movement of the second pin 41 leads to an axial movement of the sliding sleeve 39 which, because of the first pin 36, then leads to a rotational movement of the rotatable marking sleeve 34. Thus synchronously with the swivelling of the deflecting prism 7, because of a rotation of the actuating element 16, the rotatable marking sleeve 34 and thus the rotatable marking stop 32 are rotated relative to the optics tube 10 and thus relative to the fixed marking stop 31.

Figure 13:
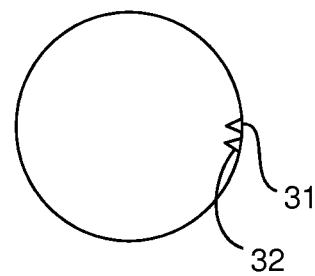
FIG. 13 is a representation explaining the fixed and rotatable marking stop.

If the user rotates the endoscope shaft 3 90° to the right (by rotating the middle section 26 relative to the main part 19) compared with the position shown in FIG. 11, the draw tube 15 is also rotated 90° to the right, whereby the actuating element 16 is also rotated to the right via the bolt 22. This leads to a rotation of the rotatable marking sleeve 34 90° to the right. As the fixed marking sleeve 33 is also rotated 90° to the right because of the rotation of the endoscope shaft 3, a user sees the two marking stops 31, 32 in the position shown in FIG. 13 when observing the image. The user can thus immediately detect the rotation position of the endoscope shaft of 90° and the direction of view of 10°.

Figure 14:
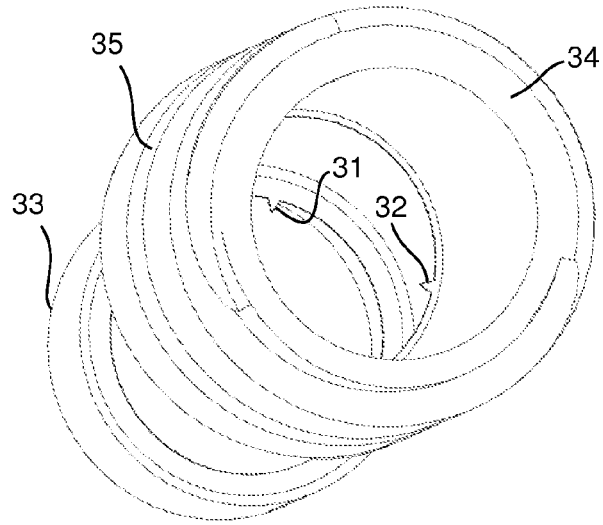
FIG. 14 is a perspective exploded representation of the two marking sleeves.

The two marking sleeves 33 and 34 are shown enlarged in FIG. 14 in a perspective exploded representation. The marking stops 31, 32 can be clearly seen in this representation.

The entire mechanism for rotating the rotatable marking stop 32 is laid out here as a reduction gear mechanism, with the result that a rotation of the actuating element 16 by a predetermined angle of rotation leads to a rotation of the rotatable marking stop 32 in which the angle of rotation is smaller than the predetermined angle of rotation. The reduction gear mechanism structure is chosen here, as the necessary axial displacement of the draw tube 15 to swivel the deflecting prism 7 requires an angle of rotation of the actuating element 16 which is greater than the desired maximum angle of rotation of the rotatable marking stop 32 or of the rotatable marking sleeve 34.

Thus it is possible to set the swivel position of the prism 7 very precisely, as a relatively large angle of rotation of the actuating element 16 is necessary in order to swivel the deflecting prism by a predetermined angle. Although the reduction gear mechanism is laid out such that the angular separation between the two marking stops 31 and 32 corresponds specifically to the angle of the set direction of view 5, a representation can nevertheless be achieved which is meaningful to the user.

The outside of the actuating element 16 can be ergonomically designed. Thus recesses 45 which guarantee a secure hold are visible in the representation of FIG. 1 and also in the representation of FIG. 7.

Figure 15:
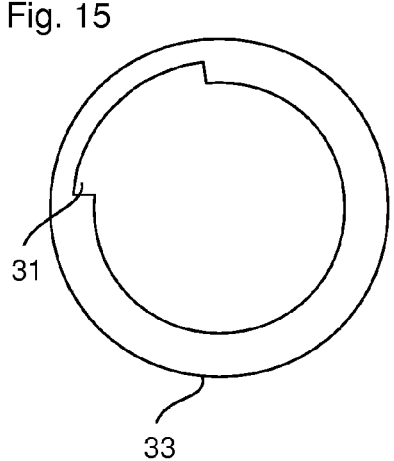
FIG. 15 is a schematic view of a variant of the fixed marking sleeve.
Figure 16:
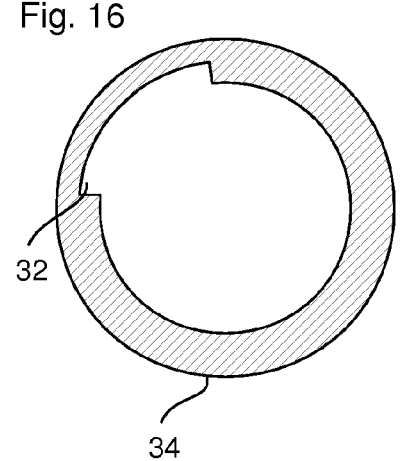
FIG. 16 is a schematic representation of a variant of the rotatable marking sleeve.
Figure 17:
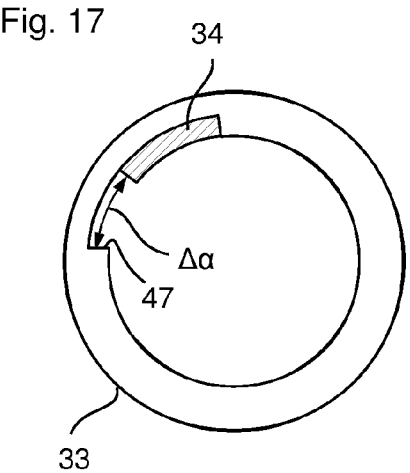
FIG. 17 is a schematic view explaining the type of representation of the two marking stops when observing the imaging of the imaging optics.

As already mentioned, the marking stops 31 and 32 can also have other forms. A top view of a variant of the fixed marking sleeve 33 is shown in FIG. 15. The ring-section-shaped recess serves as fixed marking stop 31. In FIG. 16 a top view of a variant of the rotatable marking sleeve 34 is shown, wherein in the same way as with the fixed marking sleeve 33 the ring-section-shaped recess forms the rotatable marking stop 32. In order to be able to distinguish between the two marking sleeves in the representation, the rotatable marking sleeve 34 is shaded. On the basis of the described arrangement of the two marking sleeves 33 and 34 a rotation of the rotatable marking sleeve 34 relative to the fixed marking sleeve 33 leads to the angular separation ▯ between both ring-section-shaped recesses or between both marking stops 31 and 32 changing (as is shown in FIG. 17). This angular separation ▯ then shows the observer in turn the swivel position of the deflecting prism 7 in the image. The bottom edge 47 shows e.g. the rotation position of the endoscope shaft 3.

The above disclosure is related to the detailed technical contents and inventive features thereof. People skilled in this field may proceed with a variety of modifications and replacements based on the disclosures and suggestions of the invention as described without departing from the characteristics thereof. Nevertheless, although such modifications and replacements are not fully disclosed in the above descriptions, they have substantially been covered in the following claims as appended.

What is claimed is:

1. Endoscope, comprising:
a handle;
an endoscope shaft connected to the handle;
imaging optics arranged in the endoscope shaft with which an object located in the direction of view of the imaging optics in front of the endoscope shaft is imaged as an image and which has a swivellably housed deflecting element to set the desired direction of view, said deflecting element is positioned at the distal end of the endoscope shaft facing away from the handle; and
an actuating element attached to the handle which is mechanically connected to the deflecting element and with which the swivel position of the deflecting element can be changed in order to set a desired direction of view,
wherein a first marking stop is provided which is mechanically connected to the actuating element such that the first marking stop is movable synchronously with a change in the swivel position of the deflecting element and the first marking stop displays a visible position indication through the imaging optics of the set direction of view, and
wherein the endoscope shaft is rotatably housed in the handle and has a second marking stop which is connected in rotation-resistant manner to the endoscope shaft and which displays the rotation position of the endoscope shaft by means of its visible position when observing the image.

2. The endoscope according to claim 1, wherein the actuating element is rotatably housed on the handle.

3. The endoscope according to claim 1, wherein the position of the first marking stop relative to the position of the second marking stop displays the set direction of view when observing the image.

4. The endoscope according to claim 3, wherein, the first marking stop is configured such that when it moves, its angular separation from the second marking stop is changed in order to display the direction of view by means of the angular separation.

5. The endoscope according to claim 1, wherein the actuating element is connected to the first marking stop via a reduction gear mechanism.

6. The endoscope according to claim 5, wherein the reduction gear mechanism converts a rotation of the actuating element into an axial movement and the axial movement into a rotational movement of the first marking stop.

7. The endoscope according to claim 1, wherein the first marking stop is positioned in the area of the field stop of the imaging optics.

8. The endoscope according to claim 1, wherein the first marking stop is rotatably housed relative to the imaging optics.

9. The endoscope according to claim 1, wherein a sliding element, the proximal end of which is connected to the actuating element and the distal end of which has a screening section, is arranged displaceable in the endoscope shaft, wherein an actuation of the actuating element leads to a displacement of the sliding element, and wherein the distal end of the sliding element is connected to the deflecting element such that a displacement of the sliding element brings about a change in the swivel position of the deflecting element and simultaneously a displacement of the screening section, in order to achieve, at the same time as setting the desired direction of view, a scattered-light screening for the area between the deflecting element and an optical element following the deflecting element of the imaging optics.

10. An endoscope, comprising:

a handle;

an endoscope shaft connected to the handle;

imaging optics arranged in the endoscope shaft with which an object located in the direction of view of the imaging optics in front of the endoscope shaft is imaged as an image and which has a swivellably housed deflecting element to set the desired direction of view, said deflecting element is positioned at the distal end of the endoscope shaft facing away from the handle; and an actuating element attached to the handle which is mechanically connected to the deflecting element and with which the swivel position of the deflecting element can be changed in order to set a desired direction of view, wherein a first marking stop is provided by a marking sleeve disposed within the handle, the first marking stop being mechanically connected to the actuating element such that the first marking stop is movable synchronously with a change in the swivel position of the deflecting element to provide a visual indication of the swivel position of the deflecting element, and wherein the endoscope shaft is rotatably housed in the handle and has a second marking stop which is connected in rotation-resistant manner to the endoscope shaft and which displays the rotation position of the endoscope shaft by means of its visible position when observing the image.

11. The endoscope according to claim 10, wherein the actuating element is rotatably housed on the handle.

12. The endoscope according to claim 10, wherein the position of the first marking stop relative to the position of the second marking stop displays the set direction of view when observing the image.

13. The endoscope according to claim 12, wherein, the first marking stop is configured such that when it moves, its angular separation from the second marking stop is changed in order to display the direction of view by means of the angular separation.

14. The endoscope according to claim 10, wherein the actuating element is connected to the first marking stop via a reduction gear mechanism.

* * * * *